(12) United States Patent
Torimoto

(10) Patent No.: US 6,399,113 B1
(45) Date of Patent: Jun. 4, 2002

(54) LAWN PESTICIDES AND PROCESSES

(76) Inventor: Hajime Torimoto, 3-42 Yasu-cho, Ogaki City, Gifu (JP)

( * ) Notice: Subject to any disclaimer, the term of this patent is extended or adjusted under 35 U.S.C. 154(b) by 0 days.

(21) Appl. No.: 09/654,477

(22) Filed: Sep. 1, 2000

(30) Foreign Application Priority Data

Sep. 1, 1999 (JP) ............................................ 11-247979
Jun. 21, 2000 (JP) ...................................... 2000-186347

(51) Int. Cl.[7] ........................ A61K 35/78; A01N 25/00
(52) U.S. Cl. ...................... 424/725; 424/742; 424/770; 424/405
(58) Field of Search ................................ 424/742, 770, 424/725, 405

(56) References Cited

U.S. PATENT DOCUMENTS 5,073,545 A * 12/1991 Arima et al.
5,328,914 A * 7/1994 Hocquaux et al.
5,696,169 A * 12/1997 Otsu et al.
5,700,449 A * 12/1997 Katayama et al.
6,136,778 A * 10/2000 Kamiya

FOREIGN PATENT DOCUMENTS

JP 61271398 * 12/1986
JP 10147796 * 6/1998

* cited by examiner

*Primary Examiner*—Christopher R. Tate
(74) *Attorney, Agent, or Firm*—Clark Wilson

(57) ABSTRACT

The provision of a lawn pesticide, its manufacturing process and pest extermination processes, that is water soluble, capable of being diluted in water, capable of being applied in concentrations appropriate to the environment of the treatment site and the development of the lawn, and can demonstrate prophylactic properties on lawns. The lawn pesticide is constituted from refined oils extracted from the botanical matter of the hinoki family and an amino acid derived surfactant solution, the two components are stirred and mixed, left to mature for at least two weeks at room temperature, and the refined oils extracted from the botanical matter of the hinoki family are uniformly dispersed in the water by the amino acid derived surfactants. The refined oils extracted from the botanical matter of the hinoki family contain substances such as hinoki thiol, which possesses antibacterial, bactericidal and insecticidal properties. Compared with standard chemically synthesized surfactants, the biodegradability of the amino acid derived surfactants is high. It is desirable to combine the refined oils extracted from the botanical matter of the hinoki family and the amino acid derived surfactant solution at a ratio within the range of 1:5 to 1:10.

12 Claims, 1 Drawing Sheet

LAWN PESTICIDES AND PROCESSES

FIELD OF THE INVENTION

The present invention is a lawn pesticide, and its manufacturing processes and pest extermination processes, that exterminates pests that occur on lawns on golf courses, sports turf and other lawns.

BACKGROUND OF THE INVENTION

In the past, the resistance to lawn pests on lawns such as golf courses and sports turf was diminished by foot traffic and, depending upon the lawns' purposes, severe growing environments caused by trimming. As a result, rust, leaf rot and other afflictions would occur, the lawn would wither and the aesthetic appeal of the lawn would be lost.

To eliminate said various diseases and disease causing pests, synthetic agrochemicals are being applied to lawns. However, the application of synthetic agrochemicals kills and reduces beneficial bacteria in the soil, creating further pestilence and causing concern over the pollution of the environment around lawns and ground water.

To address this, there is the lawn pesticide and pest extermination method disclosed in the Special Extract 6-040831 report. This pest control agent has refined oils extracted from botanical matter of the hinoki family as its primary component and possesses antibacterial, bactericidal and insecticidal properties. In addition, polyoxyethylene sorbitol oleate is added as a surfactant to the refined oils extracted from the botanical matter of the hinoki family to increase its usability. These components are stirred, mixed, formulated as an emulsion, and applied to the lawn.

However, lawn pesticides formulated as emulsions in the past were not sufficiently water-soluble. Accordingly, when attempts were made to dilute them with water and use them, the water and refined oils extracted from botanical matter of the hinoki family would separate and make dilution impossible. This would impact the environment of treated areas and a problem would arise whereby it was impossible to apply the pesticide at the appropriate concentration to foster the growth of the lawn.

Moreover, since the surfactants used to formulate the lawn pesticides as emulsions are chemically synthesized, they are chemically stable and their biodegradability is low. As a result, the problem arises that after emulsions have been applied to a lawn, the surfactants remain in the surrounding soil and water runoff, and may pollute the environment.

SUMMARY OF THE INVENTION

The present invention is aimed at the problems of the past technologies. Its objectives are to provide a lawn pesticide, and its manufacturing processes and pest extermination processes, that make it possible for the emulsion to be dissolved in and diluted with water, for it to be applied at the appropriate concentrations to avoid impacting the environment of treated areas and foster the growth of lawns, and for it to function as a pesticide on lawns. The other objectives of the present invention are for it to be a lawn pesticide, and its manufacturing processes and pest extermination processes, that uses and is manufactured from naturally derived materials and can contribute to environmental conservation because of its heightened biodegradability after it has been applied to a lawn.

To achieve the said objectives, the invention of the lawn pesticide according to Claim 1 comprises refined oils extracted from botanical matter of the hinoki family and an amino acid derived surfactant solution.

The lawn pesticide incorporates the botanical matter of the hinoki family wherein the botanical matter is selected from at least one of the group consisting of Taiwan hinoki, western red cedar, *hiba arborvitae*, Taiwan hiba, Taiwan hinoki, eucalyptus and incense cedar.

The lawn pesticide may further incorporate amino acid derived surfactants wherein the amino acid derived surfactants have the chemical structure expressed below:

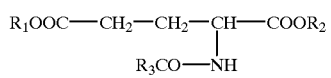

wherein $R_1$ and $R_2$ are hydrogen, alkaline metals or amino bases, and $R_3CO$ is fatty acid residues.

The manufacturing process for such lawn pesticide is one whereby refined oils extracted from the botanical matter of the hinoki family and an amino acid derived surfactant solution are combined, the resulting compound is aged for at least two weeks, and the refined oils extracted from the botanical matter of the hinoki family are uniformly dispersed into water by the amino acid derived surfactants.

The manufacturing process for the lawn pesticide may alternatively be one wherein refined oils extracted from the botanical matter of the hinoki family, an amino acid derived surfactant solution and a water-soluble thickener solution are combined and prepared as a spray, and the refined oils extracted from the botanical matter of the hinoki family are uniformly dispersed into the water by the amino acid derived surfactants and the water-soluble thickener.

The manufacturing process for the lawn pesticide may be one wherein ethanol or methanol is added to said compound and spray.

The method of exterminating lawn pests may be by diluting the lawn pesticide in water and sprinkling it over a lawn.

Detailed Description of the Invention

Figure 1:
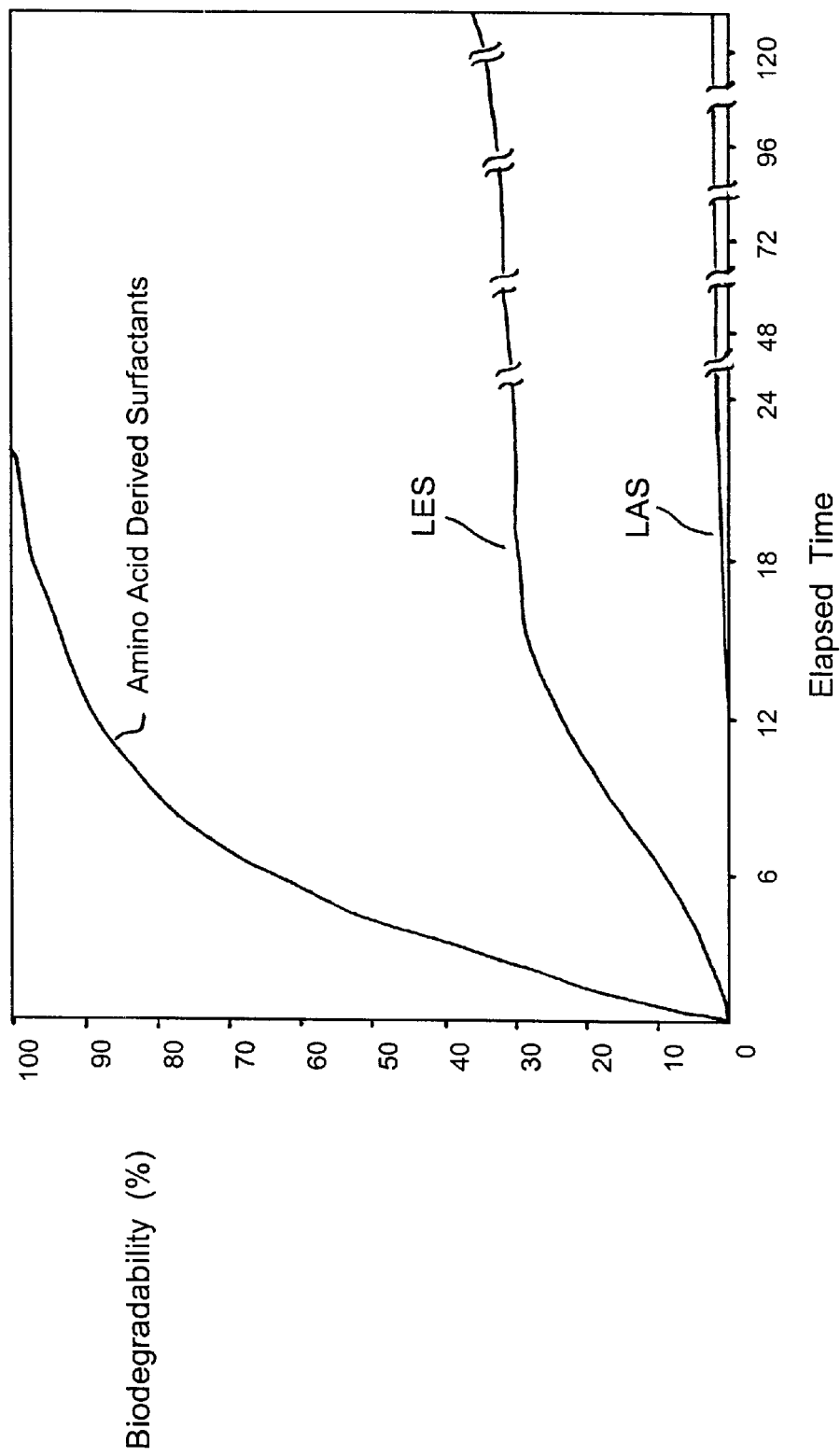
FIG. 1 is a graph showing the biodegradability of the amino acid derived surfactants over time.

The following provides a detailed description of the form in which the present invention is utilized.

The lawn pesticide comprises refined oils extracted from the botanical matter of the hinoki family (hereafter refined oil extract) and an amino acid derived surfactant solution, and the refined oil extract is uniformly dispersed in the water by the amino acid derived surfactants.

A least one of the group consisting of Taiwan hinoki, western red cedar, *Hiba arborvitae*, Taiwan hiba, Taiwan hinoki, eucalyptus and incense cedar is used as naturally derived botanical matter of the hinoki family, and every part of the leaves, stems and tissue of these plants can be utilized. Furthermore, the refined oil extract can be obtained by a steam or dry distillation process. Moreover, since no chemicals are added during the extraction process for the refined oil extract, a completely naturally derived, refined oil extract, which does not include any chemical substances, can be obtained.

Said refined oil extracts contain such substances as thujic acid, which has an antibacterial effect, thujaplicin, which has a bactericidal effect, methyl thujate, which causes pestilent insects to avoid it, and tropolone compounds, which have bactericidal and antibacterial effects. β(beta)-thujaplicinol 1, γ(gamma)-thujaplicin, β(beta)-thujaplicin 1 (hinoki thiol), α(alpha)-thujaplicin 1, and β(beta)-dolabrin are among the tropolone compounds.

Among the botanical matter of the hinoki family, the refined oil extract of the western red cedar comprises hinoki thiol amounting to 68.5% by weight, thujic acid amounting to 10.4% by weight and methyl thujate amounting to 21.1.% by weight. Western red cedar contains a higher content of hinoki thiol in comparison with other wood. Accordingly, it is desirable to use the refined oil extract of western red cedar in the lawn pesticide.

As a naturally derived amino acid derived surfactant, the substance having the structure expressed below is utilized.

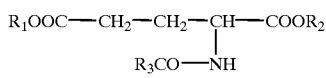

In this chemical formula, $R_1$ and $R_2$ represent hydrogen, alkaline metals or amino bases, and $R_3CO$ represents fatty acid residues. Sodium is desirable as the alkaline metal and a triethanolamine group as the amino base.

Sodium N-cocoacyl-L-glutamate (palm oil derivative), sodium N-lauroyl-L-glutamate (palm oil derivative), sodium N-cyl($C_{12, 14}$)-L-glutamate (hardened beef fat and palm oil derivative), sodium N-stearoyl-L-glutamate (hardened beef fat derivative), triethanolamine N-acyl ($C_{12, 14}$)-L-glutamate (distilled palm oil derivative), disodium N-stearoyl-L-glutamate (hardened beef fat derivative), disodium N-stearoyl-L-glutamate (hardened beef fat derivative), disodium N-acyl($C_{12, 14}$)-L-glutamate (hardened beef fat and palm oil derivative), and disodium N-acyl($C_{12, 14}$)-L-glutamate (palm oil derivative) are examples.

As shown in Diagram 1, said amino acid derived surfactants have higher biodegradability than conventional chemically synthesized sodium alkylbenzene sulfate (LAS) or sodium lauryl ether sulfate (LES), ultimately biodegrading 100%. Amino acid derived surfactants also biodegrade in a shorter time than conventional surfactants.

In addition, when the amino acid derived surfactant solution is prepared from surfactants and water, it is desirable to obtain a ratio of the amino acid derived surfactants to water of 20% to 50% by weight. When the amino acid derived surfactants in said solution are less than 20% by weight, the refined oil extract and water separate in the lawn pesticide which is obtained, which is undesirable. If, on the other hand, the solution contains more than 50% amino acid derived surfactants by weight, the viscosity of the amino acid derived surfactants themselves becomes high and spraying it becomes problematic, which is undesirable. Accordingly, the separation of the water in the amino acid derived surfactant solution from refined oil extract can be prevented by the amino acid derived surfactants.

The lawn pesticide's manufacturing process and method of use will now be explained. The amino acid derived surfactant solution is added to the refined oil extract, then the two are stirred and mixed to prepare a compound. It is desirable to mix the refined oil extract and amino acid derived surfactant solution at a ratio ranging between 1:5 and 1:10. At a mix smaller than 1:5, the refined oil extract and water separates easily, which is undesirable, when water is added to the refined oil extract and amino acid derived surfactant solution compound and it is dissolved. On the other hand, a mixture greater than 1:10 is undesirable because the refined oil extract has already been sufficiently dispersed in the water by the amino acid derived surfactant solution and higher manufacturing costs are incurred.

The refined oil extract should be dispersed evenly into the water by the amino acid derived surfactant solution, and to make certain that the two components are intimately intermingled, it is desirable to allow the mixture to mature for at least two weeks at room temperature. If the maturation period is less than two weeks, the refined oil extract and water separate when the mixture is diluted with water, which is not desirable. Please note that the maturation period is dependent upon the volume of refined oil extract and amino acid derived surfactant solution added. The more added, the longer the maturation period. As a result of the above, the refined oil extract can be uniformly dispersed into water by the amino acid derived surfactant to produce a water soluble lawn pesticide.

Moreover, if ethanol or methanol is added to the aforementioned lawn pesticide, the result is a colorless, clear liquid that can also be maintained as a colorless, clear liquid over a long period of time. It is generally desirable to set the volume of the ethanol or methanol additive to within a range of 2% to 4% by weight of the lawn pesticide. However, the ethanol or methanol additive volume can be altered in relation to the lawn pesticide volume to suit the purpose of the lawn pesticide.

Moreover, if the refined oil extract, amino acid derived surfactant solution and a water-soluble thickener are mixed together, stirred and a prepared as a spray, the spray is effective as a lawn pesticide. Xanthan gum, carrageenan, gum arabic, guar gum, gellan gum and dextran are examples of the aforementioned water-soluble thickener that may be utilized. Among these examples, the use of at least one of xanthan gum or carrageenan is desirable to uniformly and quickly disperse the refined oil extract in water.

The aforementioned carrageenan is a carbohydrate extracted from red seaweed with its main constituent being galactose or galactose ester salts. Xanthan gum is a type of polysaccharide, a transparent substance that is used as a thickening and stabilizing agent in food.

It is desirable to set the volume of water-soluble thickener in the water-soluble thickener solution to within the range of 10% to 20% by weight. If less than 10% by weight is used, it is difficult to get the refined oil extract to disperse in the water in the resulting lawn pesticide, which is undesirable. On the other hand, if more than 20% by weight is used, the refined oil extract is already uniformly dispersed in the water by the water-soluble thickener and the amino acid derived surfactants, and is water soluble, incurring increased manufacturing costs.

By mixing the water-soluble thickener solution with the refined oil extract and amino acid derived surfactant solution and preparing them as a spray, the refined oil extract is completely dispersed in the water in the solution by the water-soluble thickener and the amino acid derived surfactants. Therefore, the refined oil extract can be uniformly dispersed in water without having to allow the spray to mature for two weeks. In addition, the aforementioned water-soluble thickeners are also 100% biodegradable.

Moreover, if ethanol or methanol is added to the aforementioned spray, the result is a colorless, clear liquid that can also be maintained as a colorless, clear liquid over a long period of time. It is generally desirable in this case to set the volume of the ethanol or methanol additive to within a range of 2% to 4% by weight of the lawn pesticide. However, the ethanol or methanol additive volume can be altered in relation to the lawn pesticide volume to suit the purpose of the lawn pesticide.

It is desirable to mix the water-soluble thickener solution with the refined oil extract so that the ratio of the water-soluble thickener solution falls within the range of 1:2 to 1:4. If the ratio is made smaller than 1:2, the refined oil extract separates easily from the water when water is added to dilute the lawn pesticide, which is undesirable. If, on the other hand, the ratio is made larger than 1:4, the refined oil extract is already sufficiently dispersed in the water, and is water soluble, incurring increased manufacturing costs When the lawn pesticide obtained by either of the two methods above is used, for example as a lawn pesticide containing 10% refined oil extract by weight, it is desirable to dilute it in water at a dilution ratio within the range of 500–6500 times. If the dilution ratio is less than 300 times, the refined oil extract composition is too strong and the lawn tends to wither, which is undesirable. If, on the other hand, the dilution ratio exceeds 6500 times, the refined oil extract is too dilute and its pesticide functionality is lowered, which is undesirable. Please note that the dilution ratio depends upon the refined oil extract content and changes.

And when the lawn pesticide is diluted in water, the refined oils extracted from botanical matter of the hinoki family can be made sufficiently water-soluble by the amino acid derived surfactants derived from natural sources or by amino acid derived surfactants and water-soluble thickeners, making the lawn pesticide soluble in water.

To protect grass from disease and pests when it is sprouting—for example for use of a lawn pesticide containing 10% refined oil extract by weight—it is desirable to dilute it in water at a dilution ratio within a range of 1000–5000 times. To give it the effect of avoiding the developing areas of the lawn—for example with a lawn pesticide comprising 10% refined oil extract by weight—it is desirable to dilute it in water at a dilution ratio within a range of 500–1000 times.

The lawn pesticide so obtained can be applied to the lawn with a sprayer, spray gun or atomizer. The lawn pesticide can also be applied to the lawn with a watering can, etc.

The lawn pesticide obtained with the aforementioned methods has antibacterial, bactericidal, insecticidal and other properties through hinoki thiol and other substances. In addition, since this lawn pesticide is manufactured only from refined oil extract and a amino acid derived surfactant solution or from refined oil extract, an amino acid derived surfactant solution and water-soluble thickener solution, it is constituted entirely from naturally derived materials. Moreover, compared with chemically synthesized surfactants and thickeners, the biodegradability of the amino acid derived surfactants and water-soluble thickeners is high. As a result, the amino acid derived surfactants and water-soluble thickeners are prevented from remaining in the soil or drain water after the lawn pesticide has been applied to a lawn. In addition, the ethanol or methanol vaporizes, preventing it from accumulating in the soil or drain water.

The following sets down the effects that can be obtained by carrying out the applications described above.

With the amino acid derived surfactants, the refined oil extract demonstrates adequate solubility in water. Because of this, the solubility is higher when compared with emulsions in the past that used chemically synthesized polyoxyethylene sorbitol oleate additives as surfactants, and the lawn pesticide can be dissolved in water. As a result, it can be diluted and used at a concentration appropriate to the environment of the area having the lawn pesticide applied to it and to the development stage of the lawn, and it can have definite antibacterial, bactericidal and insecticidal effects. Its viscosity is also lower than previous emulsions. Accordingly, the lawn pesticide can be applied to a wide area when it is being applied.

Since the lawn pesticide is manufactured only from refined oil extracted from naturally derived materials and an amino acid derived surfactant solution, a lawn pesticide containing only naturally derived materials can be obtained. In addition, absolutely no chemicals are added when the refined oil extract is extracted. Further, the amino acid derived surfactants is more biodegradable than conventional chemically synthesized surfactants, such as sodium alkylbenzene sulfate (LAS) or sodium lauryl ether sodium sulfate (LES). As a result, the amino acid derived surfactants biodegrade completely and reliably after the lawn pesticide has been applied, preventing any chemicals or the surfactants from remaining in the surrounding soil or drain water and contributing to the preservation of the environment.

The refined oil extract contains hinoki thiol, which has antibacterial, bactericidal and insecticidal physiological activity, in a volume that is high in comparison with other woods. Accordingly, it can reliably endow a lawn pesticide with antibacterial, bactericidal and insecticidal properties.

The amino acid derived surfactants have the chemical structure expressed in formula (1). As a result, it can make the refined oil extract sufficiently soluble in water and permit the lawn pesticide to be dissolved in water.

Since the lawn pesticide can be diluted with water, and it can be easily applied using a sprayer, that procedure can be accomplished in a short period of time.

The mixture of the refined oil extract and amino acid derived surfactant solution is allowed to mature at room temperature for at least two weeks to obtain the lawn pesticide. Accordingly, the refined oil extract can be uniformly dispersed in the water by the amino acid derived surfactants, and when the lawn pesticide is diluted in water, the refined oil extract and water can be prevented from separating.

The mixing ratio of refined oil extract to the amino acid derived surfactant solution is set within the range of 1:5 to 1:10. As a result, the antibacterial, bactericidal and insecticidal properties of the lawn pesticide can be reliably manifested. In addition, the refined oil extract can be prevented from separating from the water. Furthermore, it prevents excess amino acid derived surfactants from being added and stops manufacturing costs from mounting.

For example, in the case of a lawn pesticide containing 10% refined oil extract by weight, the water dilution ratio would be set to 500–6500 times. This will enable the refined oil extract to be appropriately diluted and reliably demonstrate its antibacterial, bactericidal and insecticidal properties on the lawn.

By mixing the refined oil extract, amino acid derived surfactant solution and water-soluble thickener solution together, the refined oil extract can be uniformly dispersed in the water by the amino acid derived surfactants and water-soluble thickener even if the compound is not matured for two weeks. Accordingly, the manufacturing time for the lawn pesticide can be shortened.

Because the water-soluble thickeners are naturally derived substances, they biodegrade reliably after the lawn pesticide is applied, which prevents them from remaining in the surrounding soil or drain water and contributes to the preservation of the environment.

When the lawn pesticide is used, it can be prepared as a colorless, clear liquid lawn pesticide by adding ethanol or methanol. Accordingly, when the resulting lawn pesticide is applied to a lawn, the treated area will not change color and the lawn can be prevented from losing its aesthetic appeal.

EXAMPLES

The following provides examples and comparisons that further explain how the above is carried out.

Example 1

900 g of a solution of triethanolamine N-acyl ($C_{12, 14}$)-L-glutamate representing the amino acid derived surfactant solution (containing 270 g of amino acid derived surfactants) is added to 100 g of refined oil extract from western red cedar representing the refined oils extracted from botanical matter of the hinoki family, the two are stirred and mixed. Then, that mixture is matured at room temperature for 3 weeks. Thus, 1 kg of lawn pesticide with uniformly dispersed western red cedar refined oil extract in water by the triethanolamine N-acyl ($C_{12, 14}$)-L-glutamate is obtained. If this 1 kg of lawn pesticide is stirred and mixed into 999 kg of water, a 1,000-time diluted solution of lawn pesticide containing 10% by weight of western red cedar refined oil extract is obtained.

Example 2

700 g of a solution of sodium N-cyl ($C_{12, 14}$)-L-glutamate representing the amino acid derived surfactant solution (containing 210 g of amino acid derived surfactant) is added to 100 g of refined oil extract from western red cedar representing the refined oils extracted from botanical matter of the hinoki family, the two are stirred and mixed. Then, that mixture is matured at room temperature for 3 weeks. Thus, 0.8 kg of lawn pesticide with 100 g of uniformly dispersed western red cedar refined oil extract in water by the sodium N-cyl ($C_{12, 14}$)-L-glutamate is obtained. If this 0.8 kg of lawn pesticide is stirred and mixed into 999.2 kg of water, a 1,250-time diluted solution of lawn pesticide containing 12.5% by weight of western red cedar refined oil extract is obtained.

Example 3

600 g of a solution of sodium N-stearoyl-L-glutamate representing the amino acid derived surfactant solution (containing 180 g of amino acid derived surfactant) is added to 100 g of refined oil extract from *hiba arborvitae* representing the refined oils extracted from botanical matter of the hinoki family, the two are stirred and mixed. Then, that mixture is matured at room temperature for 3 weeks. Thus, 0.7 kg of lawn pesticide with 100 g of uniformly dispersed *hiba arborvitae* refined oil extract in water by the sodium N-stearoyl-L-glutamate is obtained. If this 0.7 kg of lawn pesticide is stirred and mixed into 999.3 kg of water, a 1,420-time diluted solution of lawn pesticide containing 14% by weight of *hiba arborvitae* refined oil extract is obtained.

Test of Lawn Disease Prevention

The lawn pesticides obtained in examples 1–3 and bark compost were applied to an area that was to be reseeded, and after the area was prepared for planting, the lawn was seeded. Subsequently, the state of the lawn was observed visually. As a result, diseases such as brown patches (*Rhizoctonia solani*), red blister disease (*Pythium aphanidermatum*), pythium blight (*Pythium vanterpoolii, P. periplocum, P. graminicola*), dollar spots (*Sclerotinia homoeocarpa*), fairy rings, withering disease (*Curvularia geniculatum, Helminthosporium geniculatum*), rust disease (*Puccinia zoysiae*), and spring balding disease (*Pythium vanterpoolii, P. periplocum, P. graminicola*), were not observed.

Test of Lawn Germination

The lawn pesticide obtained in Example 1 was diluted 1,000 times (western red cedar refined oil extract diluted 10,000 times) and 5,000 times (western red cedar refined oil extract diluted 50,000 times) and prepared as a soil improvement spray. The soil improvement spray was then applied and the sprouting status of the lawn observed. The lawn was observed to sprout. Thus, as a lawn pesticide applied as a soil improvement spray, it can be expected to control insects that would have eaten the young leaves of the grass.

Repellant Test

The lawn pesticide obtained in Example 1 was diluted 500 times (western red cedar refined oil extract diluted 5,000 times) and applied to a lawn. As a result, earthworms bolted out of the treated soil. In addition, the lawn pesticide was diluted 1,000 times (western red cedar refined oil extract diluted 10,000 times) and applied to the lawn. As a result, hardly any worm casings were seen for several days after. Thus, the repellant properties of the lawn pesticide on worms and other insects can be demonstrated.

Example 4, Example 5 and Control Example 1

In Example 4, the lawn pesticide obtained in Example 1 was applied to a cloth, the cloth was inoculated with bacteria and the antibacterial action was measured. In Example 5, the lawn pesticide obtained in Example 1 was applied to a cloth, the cloth was rinsed 10 times, the cloth was inoculated with bacteria and the antibacterial action was measured. In Control Example 1, a cloth that had not had the lawn pesticide applied to it was inoculated with bacteria and the antibacterial action was measured.

The antibacterial test was based on the Antibacterial Testing Method for Textile Products specified in JIS L 1902 (Japanese Industrial Standards). In Example 4, first the lawn pesticide obtained in Example 1 was applied to a cloth. Next, a population of $2.1 \times 10_4$ (logA 4.3) yellow grape micrococcus (*Staphylococcus aureus* ATCC 6538P) bacteria was inoculated. The bacteria were cultivated for 18 hours and the population after the elapse of 18 hours was measured (logC 1.3 or less).

In Example 5, first the lawn pesticide obtained in Example 1 was applied to a cloth. Next, after that cloth was rinsed 10 times, a population of $2.1 \times 10^4$ (logA 4.3) yellow grape micrococcus bacteria was inoculated the same as in Example 4, the bacteria were cultivated for 18 hours, and the population measured (logC 1.3 or less) after the elapse of 18 hours.

In Control Example 1, a population of $2.1 \times 10^4$ (logA 4.3) yellow grape micrococcus bacteria was inoculated the same as in Example 4 without the cloth having any lawn pesticide applied to it. The bacteria were cultivated for 18 hours and the population after the elapse of 18 hours was measured (logB 6.3).

Further, the bacteriostatic factor, which expresses the efficacy at controlling the propagation of the yellow grape micrococcus, and the bactericidal factor, which expresses the efficacy at hindering the development of the yellow grape micrococcus and controlling its propagation, were measured for Example 4, Example 5 and Control Example 1. The bacteriostatic factor fell from logb to logC as measured and the bactericidal factor fell from logA to logC as measured.

These data are shown in Chart 1.

CHART 1

|  | Live Bacteria Count | Bactericidal Factor | Bacteriostatic Factor |
| --- | --- | --- | --- |
| Example 4 | $\leq 2.1 \times 10 (\leq \log C\ 1.3)$ | $\geq 3.0$ | $\geq 5.0$ |
| Example 5 | $\leq 2.1 \times 10 (\leq \log C\ 1.3)$ | $\geq 3.0$ | $\geq 5.0$ |
| Control Example 1 | $2.1 \times 10^6 (\log B\ 6.3)$ | — | — |

As indicated by Chart 1, the antibacterial evaluation standards were attained since the bactericidal and bacteriostatic factors were greater than 2.2 in examples 4 and 5. Thus, the lawn pesticide has demonstrated its antibacterial properties.

Examples 6–9

In Example 6, a lawn pesticide containing 10% by weight western red cedar raw oil and refined oil extract was tested for bactericidal action on yellow grape micrococcus (*Staphylococcus aureus* IFO 12732: gram-positive cocci. In Example 7, a lawn pesticide containing 10% by weight western red cedar raw oil and refined oil extract was tested for bactericidal action on colon bacillus (*Escherichia coli* IFO 3972: gram-negative cocci).

In Example 8, a lawn pesticide containing 10% by weight western red cedar raw oil and refined oil extract was tested for bactericidal action on *Pseudomonas aeruginosa* NCTC 7649: gram-negative cocci. In Example 9, a lawn pesticide containing 10% by weight western red cedar raw oil and refined oil extract was tested for bactericidal action on intestinal bacillus (*Proteus vulgaris* IFO 3045: gram-negative cocci).

The testing methods involved first the respective inoculations of 10 ml of bacteria culture media (Trypticase soy broth) for each test bacteria, then the cultivation of three generations of the bacteria from the source bacteria over 24 hours to create a fresh bacterial solution, which was diluted 100 times in a sterile saline solution to create the respective inoculation solutions.

Next, a lawn pesticide containing 10% by weight western red cedar raw oil and refined oil extract was diluted in a bacterial culture medium for measuring sensitivity to step its concentration down 10 times and was prepared as a bullion bacteria culture media for measuring the sensitivity of the test substances.

Then, 0.05 ml of each of the inoculation solutions mentioned above was added to the bullion bacteria culture media for measuring the sensitivity of the test substances to make the test solutions, which were cultivated for 24 hours at 37° C. As a positive control, the inoculation solutions were added to 1 ml of the bullion bacteria culture media for measuring sensitivity (not containing any lawn pesticide containing 10% by weight western red cedar raw oil and refined oil extract) and cultivated under the same conditions. Then, the concentrations when the respective bullion bacteria culture media for measuring the sensitivity of the test substances began to cloud were observed for comparison against the bacteria culture media for measuring sensitivity. Those concentrations were the minimum concentrations (minimum concentration for the prevention of propagation) that would no longer support the propagation of each test bacteria.

In addition, a 0.05 ml test solution of each of the minimum concentrations for the prevention of propagation was extracted and added to 1 ml of the bacteria culture media for measuring sensitivity and cultivated under the same conditions. Then, the minimum concentration under which the propagation of bacteria could not be detected was observed. Those concentrations were the minimum concentration (minimum bactericidal concentration) that could kill each test bacteria. Those results are displayed in Chart 2.

CHART 2

|  | Test Category | Raw Oil | Refined Oil Extract |
| --- | --- | --- | --- |
| Example 6 | Minimum Concentration for the Prevention of Propagation (%) | 0.0039 | 0.0156 |
|  | Minimum Bactericidal Concentration (%) | 0.0078 | 0.0156 |
| Example 7 | Minimum Concentration for the Prevention of Propagation (%) | 0.0625 | 0.125 |
|  | Minimum Bactericidal Concentration (%) | 0.25 | 0.25 |
| Example 8 | Minimum Concentration for the Prevention of Propagation (%) | 0.0625 | 0.0625 |
|  | Minimum Bactericidal Concentration (%) | 1 | 0.5 |
| Example 9 | Minimum Concentration for the Prevention of Propagation (%) | 0.0625 | 0.0625 |
|  | Minimum Bactericidal Concentration (%) | 1 | 0.25 |

As shown in Chart 2, a lawn pesticide containing 10% by weight western red cedar raw oil or refined oil extract can be shown to demonstrate bactericidal properties at extremely low concentrations.

Food Preservative Test

Changing the concentration of western red cedar refined oil extract in the lawn pesticide obtained in Example 1, its food preservative properties were measured.

As for the measuring method, western red cedar refined oil extract was diluted with water so that it would have a content of 0.05%, 0.1%, 0.5%, 0.8%, 1.0% by weight, variously. Then, the various solutions were poured into flasks into which slices of raw swordfish had been placed to serve as the test foodstuff. Then, after the flasks had been left for 4 hours, the bacteria on the swordfish slices, such as *Staphylococcus aureus*, were enumerated. As a control, swordfish slices that had not had western red cedar refined oil extract poured on them were enumerated for bacteria, such as *Staphylococcus aureus*, after 4 hours. Those results are included in Chart 3.

CHART 3

| Western Red Cedar Concentration (% by Weight) | Bacteria Count (Individual) |
| --- | --- |
| 0 | 480,000 |
| 0.05 | 130,000 |
| 0.1 | 210,000 |
| 0.5 | 100,000 |
| 0.8 | 72,000 |
| 1 | 100,000 |

As shown in Chart 3, it can be conferred to have food-preserving properties since it demonstrated that it reduced the count of bacteria, such as *Staphylococcus aureus*, in comparison with the control.

Example 10

First, 500 g of a solution of triethanolamine N-acyl ($C_{12, 14}$)-L-glutamate representing the amino acid derived surfactant solution (containing 150 g of amino acid derived surfactant), and a water-soluble thickener solution comprising 40 g of carrageenan and 310 g of water are mixed together to prepare a solution. Next, 150 g of Taiwan hinoki refined oil extract representing the refined oils extracted from botanical matter of the hinoki family is added to the solution at room temperature, the two are stirred and mixed to prepare a spray. The result is 1.0 kg of lawn pesticide in the form of a yellowish brown paste with 150 g of uniformly dispersed Taiwan hinoki refined oil extract in the water. Then 6 g of this lawn pesticide is stirred and mixed into 994 g of water, to obtain a 165-time diluted solution of lawn pesticide containing 0.09% by weight of Taiwan hinoki refined oil extract.

Further, 6 g of the aforementioned lawn pesticide, 694 g of water, and 300 g of ethanol are mixed and stirred, to obtain 1 kg of a colorless, clear lawn pesticide containing 0.054% by weight of Taiwan hinoki refined oil extract.

Example 11

First, 500 g of a solution of sodium N-cyl ($C_{12, 14}$)-L-glutamate representing the amino acid derived surfactant solution (containing 150 g of amino acid derived surfactant), and a water-soluble thickener solution comprising 40 g of xanthan gum and 310 g of water are mixed together to prepare a solution. Next, 150 g of western red cedar refined oil extract representing the refined oils extracted from botanical matter of the hinoki family is added to the solution at room temperature, the two are stirred and mixed to prepare a spray. The result is 1.0 kg of lawn pesticide in the form of a yellowish brown paste with 150 g of uniformly dispersed western red cedar refined oil extract in the water. Then 6 g of this lawn pesticide is stirred and mixed into 994 g of water, to obtain a 165-time diluted solution of lawn pesticide containing 0.09% by weight of western red cedar refined oil extract.

Further, 6 g of the aforementioned lawn pesticide, 694 g of water, and 300 g of ethanol are mixed and stirred, to obtain 1 kg of a colorless, clear lawn pesticide containing 0.054% by weight of western red cedar refined oil extract.

Example 12

First, 500 g of a solution of sodium N-stearoyl-L-glutamate representing the amino acid derived surfactant solution (containing 150 g of amino acid derived surfactant), and a water-soluble thickener solution comprising 40 g of carrageenan and 310 g of water are mixed together to prepare a solution. Next, 150 g of refined oil extract from *hiba arborvitae* representing the refined oils extracted from botanical matter of the hinoki family is added to the solution at room temperature, the two are stirred and mixed to prepare a spray. The result is 1.0 kg of lawn pesticide in the form of a yellowish brown paste with 150 g of uniformly dispersed *hiba arborvitae* refined oil extract in the water. Then 6 g of this lawn pesticide is stirred and mixed into 994 g of water, to obtain a 165-time diluted solution of lawn pesticide containing 0.09% by weight of *hiba arborvitae* refined oil extract.

Further, 6 g of the aforementioned lawn pesticide, 694 g of water, and 300 g of ethanol are mixed and stirred, to obtain 1 kg of a colorless, clear lawn pesticide containing 0.054% by weight of *hiba arborvitae* refined oil extract.

Example 13

First, 500 g of a solution of sodium N-cyl ($C_{12, 14}$)-L-glutamate representing the amino acid derived surfactant solution (containing 150 g of amino acid derived surfactant), and a water-soluble thickener solution comprising 40 g of xanthan gum and 310 g of water are mixed together to prepare a solution. Next, 150 g of refined oil extract from incense cedar representing the refined oils extracted from botanical matter of the hinoki family is added to the solution at room temperature, the two are stirred and mixed to prepare a spray. The result is 1.0 kg of lawn pesticide in the form of a yellowish brown paste with 150 g of uniformly dispersed incense cedar refined oil extract in the water.

Further, 6 g of the aforementioned lawn pesticide, 694 g of water, and 300 g of ethanol are mixed and stirred, to obtain 1 kg of a colorless, clear lawn pesticide containing 0.054% by weight of incense cedar refined oil extract.

In addition, some technical concepts derived from the aforementioned examples are noted below.

The lawn pesticide according to any of claims 1 to 4 whereby said refined oils extracted from the botanical matter of the hinoki family and said amino acid derived surfactant solution are combined at a ratio ranging between 1:5 and 1:10.

If formulated in this way, the antibacterial, bactericidal and insecticidal and other properties of the lawn pesticide can be demonstrated. In addition, when the lawn pesticide is diluted with water, the separation of the refined oil extracted from the botanical matter of the hinoki family from the water can be prevented. Furthermore, the excess addition of amino acid derived surfactant solution is avoided, making it possible to avoid increased manufacturing costs.

The lawn pesticide wherein the said refined oils extracted from the botanical matter of the hinoki family are refined oils extracted from western red cedar. If formulated in this way, the hinoki thiol contained in the refined oils extracted from western red cedar is present in a volume high in comparison with other woods. As a result, it can reliably endow the lawn pesticide with prophylactic properties, such as antibacterial, bactericidal and insecticidal properties.

The method of exterminating lawn pests whereby a lawn pesticide containing 10% by weight of said refined oils extracted from the botanical matter of the hinoki family is diluted with water at a dilution ratio within the range of 500 to 6500 times and used. If formulated in this way, the lawn pesticide can be diluted to a level appropriate to the environment in which it will be applied and to the growing conditions of the lawn, and it can reliably exert antibacterial, bactericidal and insecticidal effects on the lawn.

The method of exterminating lawn pests whereby a lawn pesticide containing 10% by weight of said refined oils extracted from the botanical matter of the hinoki family is diluted with water at a dilution ratio within the range of 1000 to 5000 times and used. If formulated in this way, the pests that eat the lawn sprouts are removed by the lawn pesticide and the obstacles to the sprouting of the lawn can be removed.

The method of exterminating lawn pests whereby a lawn pesticide containing 10% by weight of said refined oils extracted from the botanical matter of the hinoki family is diluted with water at a dilution ratio within the range of 500 to 1000 times and used. If formulated in this way, it can have a repellant effect on insects, such as worms.

The bactericide derived from the refined oils extracted from the botanical matter of the hinoki family and an amino acid derived surfactant solution. If formulated in this way, it can effectively have a bactericidal effect on, for example, *Escherichia coli, Staphylococcus aureus, Pseudomonas aeruginosa* and *Proteus vulgaris*.

The antibacterial substance derived by stabilizing unstable items with a compound composed of refined oils extracted from the botanical matter of the hinoki family and an amino acid derived surfactant solution. If formulated in this way, it can endow an unstable item with antibacterial properties, an unstable item such as cloth, for example, which could be stabilized with the compound.

The food preservative derived from refined oils extracted from the botanical matter of the hinoki family and an amino acid derived surfactant solution. If formulated in this way, the propagation of bacteria occurring on food products can be suppressed, allowing food products to be stored for long periods of time.

The repellant derived from refined oils extracted from the botanical matter of the hinoki family and an amino acid derived surfactant solution. If formulated in this way, it can demonstrate repellant properties on worms and other insects.

The lawn pesticide derived from refined oils extracted from the botanical matter of the hinoki family, an amino acid derived surfactant solution and a water-soluble thickener solution.

PROPERTIES OF THE INVENTION

As discussed above, the following outcomes can be accomplished with this invention.

Said lawn pesticide can effectively act on lawns as a water soluble pesticide that can be diluted with water, and that can be applied in concentrations appropriate to the environment of the treatment site and to the growth state of the lawn. Moreover, it uses and is manufactured from naturally derived raw materials, and it can contribute to the environmental conservation because of its heightened biodegradability after treatment of the lawn.

In addition, said lawn pesticide contains a higher volume of hinoki thiol, which possesses antibacterial, bactericidal and insecticidal properties, than other wood materials. Accordingly, it can reliably endow the lawn pesticide with prophylactic properties, such as antibacterial, bactericidal and insecticidal properties.

The refined oils extracted from the botanical matter of the hinoki family in said lawn pesticide can be made sufficiently water soluble so that the lawn pesticide can be made water soluble.

With the manufacturing process for said lawn pesticide, the refined oils extracted from the botanical matter of the hinoki family can be uniformly dispersed in water by the amino acid derived surfactants, and when diluted with water, the separation of the amino acid derived surfactants and the water can be prevented.

With the manufacturing process for said lawn pesticide, the refined oils extracted from the botanical matter of the hinoki family can be rapidly and uniformly dispersed in water by the amino acid derived surfactants and water-soluble thickeners, shortening the manufacturing time for the lawn pesticide.

With the manufacturing process for said lawn pesticide, in addition, the resulting lawn pesticide can be prepared as a colorless, clear liquid, which prevents any reduction in the aesthetic appeal of the areas treated with the lawn pesticide.

With the method of exterminating lawn pests, said lawn pesticide can be diluted appropriately for the environment of the treated site and the growth state of the lawn, and its antibacterial, bactericidal and insecticidal properties can be reliably manifested.

I claim:

1. A lawn pesticide comprising:
   (a) refined oils extracted from botanical matter of the hinoki (Cupressaceae) family and,
   (b) an amino acid derived surfactant solution wherein amino acid derived surfactants comprise 20 to 50% by weight of said solution;
   wherein said refined oils are mixed with said solution at a ratio of between 1:5 and 1:10.

2. A lawn pesticide according to claim 1 wherein the said botanical matter of the hinoki family is selected from at least one of the group consisting of Taiwan hinoki (cypress), western red cedar, *hiba arborvitae*, Taiwan hiba (*hiba arborvitae*), Taiwan hinoki (cypress), and incense cedar.

3. The lawn pesticide according to claim 1 wherein said amino acid derived surfactants possess the chemical structure expressed below:

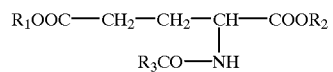

wherein, $R_1$ and $R_2$ are hydrogen, alkaline metals or amino bases, and $R_3CO$ is fatty acid residues.

4. The lawn pesticide according to claim 2 wherein said amino acid derived surfactants possess the chemical structure expressed below:

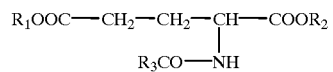

wherein, $R_1$ and $R_2$ are hydrogen, alkaline metals or amino bases, and $R_3CO$ is fatty acid residues.

5. A manufacturing process for a lawn pesticide comprising the steps of:
   (a) combining:
      (i) refined oil extracted from the botanical matter of the hinoki family and
      (ii) an amino acid derived surfactant solution wherein amino acid derived surfactants comprise 20 to 50% by weight of said solution; at a ratio of said oil to said solution of between 1:5 and 1:10; and (b) aging the combination for at least two weeks.

6. A manufacturing process for a lawn pesticide comprising the steps of:

(a) combining:
(i) refined oil extracted from the botanical matter of the hinoki family;
(ii) an amino acid derived surfactant solution wherein amino acid derived surfactants comprise 20 to 50% by weight of said amino acid derived surfactant solution; and
(iii) a water-soluble thickener solution wherein water-soluble thickener comprises 10 to 20% by weight of said water-soluble thickener solution; at a ratio of said oils to said surfactant solution of between 1:5 and 1:10 and at a ratio of said oils to said water-soluble thickener solution of between 1:2 and 1:4; and (b) preparing a spray from said combined solution.

7. The manufacturing process for the lawn pesticide according to claim 5 wherein ethanol or methanol is added to said compound.

8. The manufacturing process for the lawn pesticide according to claim 6 wherein ethanol or methanol is added to said or spray.

9. A method of eliminating lawn pests by diluting said lawn pesticide according to claim 1 in water and spraying it over a lawn.

10. A method of eliminating lawn pests by diluting said lawn pesticide according to claim 2 in water and spraying it over a lawn.

11. A method of eliminating lawn pests by diluting said lawn pesticide according to claim 3 in water and spraying it over a lawn.

12. A method of eliminating lawn pests by diluting said lawn pesticide according to claim 4 in water and spraying it over a lawn.

* * * * *